(12) United States Patent
Sendai

(10) Patent No.: US 7,477,930 B2
(45) Date of Patent: Jan. 13, 2009

(54) RADIATION EMISSION CONTROL METHOD, APPARATUS AND PROGRAM

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 131 days.

(21) Appl. No.: 11/189,742

(22) Filed: Jul. 27, 2005

(65) Prior Publication Data

US 2006/0025672 A1    Feb. 2, 2006

(30) Foreign Application Priority Data

Jul. 27, 2004   (JP)   ............... 2004-218566

(51) Int. Cl.
*A61B 5/05*   (2006.01)

(52) U.S. Cl. ..................... 600/436; 600/407

(58) Field of Classification Search ........... 378/95, 378/4–8, 15, 19, 23, 128; 600/427–428, 600/301, 473, 476
See application file for complete search history.

(56) References Cited

U.S. PATENT DOCUMENTS 7,050,537 B2 * 5/2006 Tsujii ........................ 378/95
7,177,386 B2 * 2/2007 Mostafavi et al. .......... 378/4
2004/0030235 A1   2/2004 Sasaki et al.
2004/0133102 A1 * 7/2004 Uematsu ................. 600/436

FOREIGN PATENT DOCUMENTS

| JP | 2000-201922 A | 7/2000 |
| JP | 2001-299942 A | 10/2001 |
| JP | 2002-360543 A | 12/2002 |
| JP | 2003-290184 A | 10/2003 |
| JP | 2003-290202 A | 10/2003 |
| JP | 2003-298939 A | 10/2003 |
| JP | 2004-57559 A | 2/2004 |

* cited by examiner

*Primary Examiner*—Eric F Winakur
*Assistant Examiner*—Lawrence N Laryea
(74) *Attorney, Agent, or Firm*—Sughrue Mion, PLLC

(57) ABSTRACT

A radiation emission control method, apparatus and the program capable of detecting respiratory phases of a test subject with constant accuracy and emitting radiation rays to the test subject in synchronization with an intended respiratory phase, while minimizing the radiation exposure to the subject. A test subject having a contour that varies with the respiration is optically imaged continuously by the optical image obtaining section to sequentially obtain optical images of the subject, and respiratory phases of the subject are detected simultaneously with the optical imaging by the respiratory phase detecting section based on the contour of the subject on the optical images. During the optical imaging, a radiation source is controlled by the control section such that radiation rays are emitted to the test subject when the detected respiratory phase corresponds to an intended respiratory phase of the subject.

16 Claims, 8 Drawing Sheets

RADIATION EMISSION CONTROL METHOD, APPARATUS AND PROGRAM

BACKGROUND OF THE INVENTION

1. Field of the Invention

The present invention relates to a radiation emission control method, apparatus and the program. More specifically, the present invention relates to a radiation emission control method, apparatus and the program for obtaining a radiation image of a test subject when the subject is in an intended respiratory phase.

2. Description of the Related Art

Generally, chest and abdominal radiographs, including digital images, are imaged or obtained as photographs for use to perform diagnostic image interpretations. Chest radiographs are often imaged when a patient as the test subject is in a maximum inhaled state to obtain a widest possible chest region for imaging, or they are imaged serially in each respiratory phase in order to observe the chest region under respiration. On the other hand, abdominal radiographs are often imaged when the test subject is in a maximum exhaled state to obtain a widest possible abdominal region for imaging. As described above, chest and abdominal radiographs are imaged when the test subject is in an intended respiratory phase which is dependent on the intended use.

In the mean time, in imaging a test subject when the subject is in an intended respiratory phase, it is customary that the subject is directed by the radiographer to hold the breath at the intended respiratory phase, since the subject may control its own respiratory phase.

But, if the test subject is an individual having difficulties to communicate with the radiographer, such as an infant or the like, or when radiographs are to be imaged sequentially at each respiratory phase in order to obtain a dynamic image of the test subject under respiration, it may be difficult for the test subject to hold the breath at each of the respiratory phases.

Under these circumstances, various methods for detecting respiratory phases of a test subject through some way or another are proposed for radiographing the subject in synchronization with an intended respiratory phase.

One such method is proposed as described, for example, in Japanese Unexamined Patent Publication Nos. 2003-290184, 2003-290202, and 2003-298939. The method detects respiratory phases of a test subject through a dynamic x-ray image obtained by continuously x-raying the test subject, and radiographing the test subject in synchronization with an intended respiratory phase. Another type of method is also proposed as described, for example, in U.S. Patent Application Publication No. 20040030235 and Japanese Unexamined Patent Publication Nos. 2000-201922, 2001-299942, 2002-360543 and 2004-057559. The method detects respiratory phases of a test subject by measuring the displacement of the body surface of the test subject using a distance measuring means having an LED or LD (laser diode), and radiographing the subject in synchronization with an intended respiratory phase.

The method that uses a dynamic x-ray image to detect respiratory phases of a test subject, however, has the disadvantage that the subject is exposed to an excessive amount of radiation dosage. While, in the method that detects respiratory phases of a test subject by measuring the displacement of the body surface of the subject using a distance measuring means, the position of the body surface of the subject is directly measured. Thus, it tends to have detection errors arising from the changes in the posture of the test subject, and suffers from the problem that it may not provide stable accuracy for detecting respiratory phases of the subject.

SUMMARY OF THE INVENTION

The present invention has been developed in view of the circumstances described above, and it is an object of the present invention to provide a radiation emission control method, apparatus and the program capable of detecting respiratory phases of a test subject with constant accuracy and emitting radiation to the test subject in synchronization with an intended respiratory phase, while minimizing the radiation exposure to the test subject.

Here, one seemingly similar method is proposed in Japanese Unexamined Patent Publication No. 6(1994)-054916. The method obtains a digital image by imaging the chest or abdominal region of a patient using a TV camera to detect respiratory phases of the patient based on the periodic changes in the characteristic amounts of the image, such as the density, variance value and the like, and emits radiation for medical treatment in synchronization with an intended respiratory phase. It should be noted, however, that the method described above is dissimilar to the present invention in that it uses characteristic amounts of an image, such as the densities, variance values and the like, instead of the geometry of an image as used in the present invention for detecting the respiratory phases. Further, the aforementioned method is a method of radiotherapy, while the present invention is a method of radiography.

The radiation emission control method of the present invention is a method in which optical images of a test subject having a geometric feature that varies at least partially with respiration of the subject are obtained sequentially by imaging the subject continuously, and respiratory phases of the test subject are detected simultaneously with the optical imaging based on the geometric feature of the subject on the optical images, wherein a radiation source is controlled such that radiation rays are emitted to the test subject when a respiratory phase detected corresponds to an intended respiratory phase during the optical imaging of the subject.

The radiation emission control apparatus of the present invention comprises:

an optical image obtaining means for sequentially obtaining optical images of a test subject having a geometric feature that varies at least partially with respiration of the subject by imaging the subject continuously;

a respiratory phase detecting means for sequentially detecting respiratory phases of the test subject simultaneously with the optical imaging based on the geometric feature of the subject on the optical images;

a radiation source for emitting radiation rays to the test subject; and a control means for controlling the radiation source such that radiation rays are emitted to the test subject when the respiratory phase detected by the respiratory phase detecting means corresponds to an intended respiratory phase during the optical imaging of the subject.

The program of the present invention is a program for causing a computer to perform the functions of:

a respiratory phase detecting means for sequentially receiving optical images of a test subject having a geometric feature that varies at least partially with respiration of the subject obtained by imaging the subject continuously, and sequentially detecting respiratory phases of the test subject based on the geometric feature of the subject on the optical images; and a control means for controlling a radiation source such that radiation rays are emitted to the test subject when the respiratory phase detected by the respiratory phase detecting means corresponds to an intended respiratory phase during the optical imaging of the subject.

The referent of "geometric feature" as used herein may be, for example, the contour of a test subject, a shadow region of a test subject, or a marker arranged on a test subject.

If the "geometric feature" is a "shadow region of a test subject" (e.g. a shadow region formed by a collarbone, rib or the like), the shadow region is detected as an edge within the subject image region on an optical image using an edge detecting filter (e.g. Sobel filter, Laplacian filter or the like), and respiratory phases of the subject are detected based on the changes in the position of the detected edge on the image arising from respiration of the subject. In order to know the changes in the position of the edge, it is necessary to identify which edges correspond with each other between two temporally successive optical image frames obtained continuously. In general, video rates of optical images are relatively high (e.g. 30 frames/second) so that the positions of the edge may not change significantly between the two temporally successive optical images. Thus, the edges at comparable positions between two temporally successive optical images may be deemed to correspond with each other. When detecting the changes in the edge position, the difference between two temporally successive optical images is obtained to eliminate edges that do not change in the position with the respiration, thereby the changes in the edge position become evident.

When the "geometric feature" is a "marker attached to the test subject", the marker is applied to the subject, and the marker on the optical images is detected by a known pattern recognition technology to detect respiratory phases of the subject based on the movement of the detected marker. In this case, such markers may be used as those having a sufficiently low absorption rate of radiation compared with that of a test subject and readily distinguishable on the optical images. For example, such a marker may be used as that made of a cloth material having a color (red, green, blue or the like) and a geometric shape (crisscross, star, triangle, or the like), which are not of living organisms, with a size large enough to be distinguished by the resolution of the optical imaging system. The marker is placed on a position of a test subject which is moved by respiration of the subject, such as the upper portion of the chest region, abdominal region or the like. The method of placing the marker on a moving position of a test subject by the respiration of the subject may include wearing a radiographing gown or the like having the marker fixedly attached thereto, as well as directly applying to the surface of the subject or attaching on the clothes of the subject.

The referent of "optical image" is an image obtained by optically detecting visible light rays reflected from a subject, and is different from an image obtained by detecting radiation rays transmitted through the subject.

In the radiation emission control apparatus of the present invention, the optical image obtaining means may be configured to obtain a plurality of preliminary optical images in advance by imaging the test subject continuously at least during the time period from either a maximum inhaled or exhaled state of the test subject to the other. In this case, the respiratory phase detecting means may comprise: a contour extracting means for extracting a contour that varies with respiration of the test subject from a predetermined local reference region of the preliminary optical images and optical images; a maximum displacement amount calculating means for calculating a maximum amount of displacement of the contour in the plurality of preliminary optical images; a displacement amount measuring means for sequentially detecting the displacement directions of the contour on the optical images based on the time-series optical images obtained by the optical image obtaining means, and sequentially measuring the amounts of displacement of the contour with reference to the position of the contour at the moment when the displacement direction is reversed; and a phase detecting means for detecting respiratory phases of the test subject based on the relationship of the amounts of displacement of the contour to the maximum displacement amount.

In the radiation emission control apparatus configured in the manner described above, the contour extracting means may comprise a local differential image generating means constructed to perform a subtractive operation between images within the predetermined reference region of two temporally successive optical images obtained by the optical image obtaining means to generate a local differential image that represents the difference between the images, and the contour extracting means may be configured to extract the contour based on the difference represented by the local differential image.

In the radiation emission control apparatus configured in the manner described above, the respiratory phase detecting means may further comprise: a preliminary differential image generating means constructed to perform a subtractive operation between each pair of two temporally successive preliminary optical images of the plurality of preliminary optical images to generate preliminary differential images, each representing the difference between each image pair; and a reference region setting means constructed to set a local region of the optical images that corresponds to the local region of the differential images that includes a differential region having the largest area among the differences represented by each preliminary differential image as the reference region.

Further, in the present invention, the referent of "intended respiratory phase" may be a plurality of respiratory phases included in a respiratory cycle of maximum inhaled to exhaled state of the test subject.

According to the radiation emission control method, apparatus and the program, respiratory phases of the test subject are detected using optical images obtained without any radiation exposure to a test subject. Thus, the radiation exposure to the test subject is limited only when the subject is actually radiographed, unlike the method in which a dynamic radiation image is obtained by emitting additional radiation to the test subject to detect the respiratory phases of the subject. Further, the present invention detects respiratory phases of a test subject based on the displacement of a geometric feature of the subject on the optical images. Thus, the present invention may prevent detection errors arising from the changes in the posture of a test subject, unlike the method in which an amount of displacement of the body surface of the subject is directly measured using a distance measuring means having an LED, LD or the like to detect respiratory phases of the subject. Consequently, the present invention may detect respiratory phases of a test subject with constant accuracy and emit radiation to the test subject in synchronization with an intended respiratory phase, while minimizing the radiation exposure to the test subject.

DESCRIPTION OF THE PREFERRED EMBODIMENTS

Hereinafter, embodiments of the present invention will be described in detail.

Figure 1:
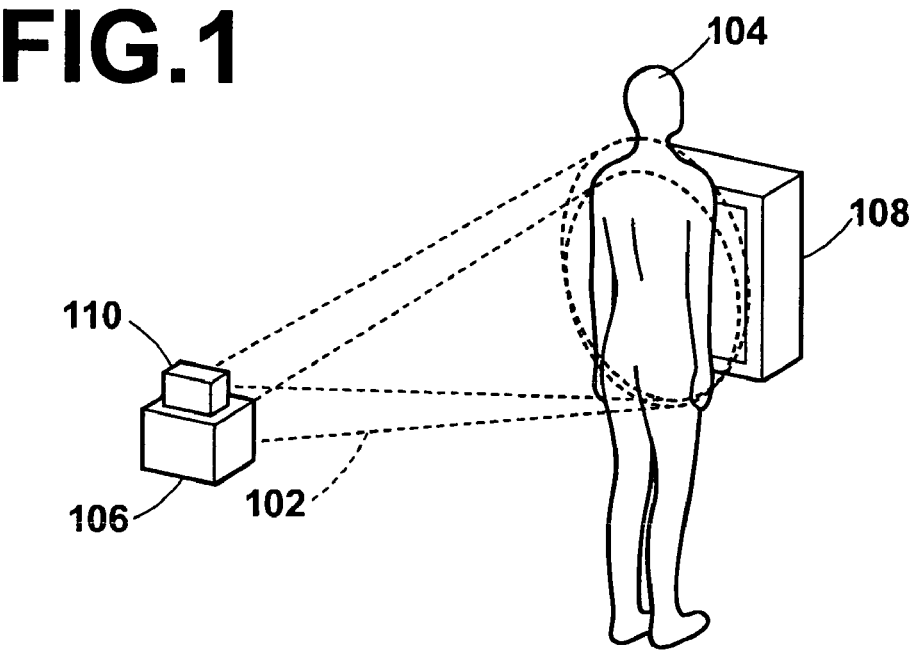
FIG. 1 is an external view of a radiographing system 100 illustrating one aspect of the external view thereof.
Figure 2:
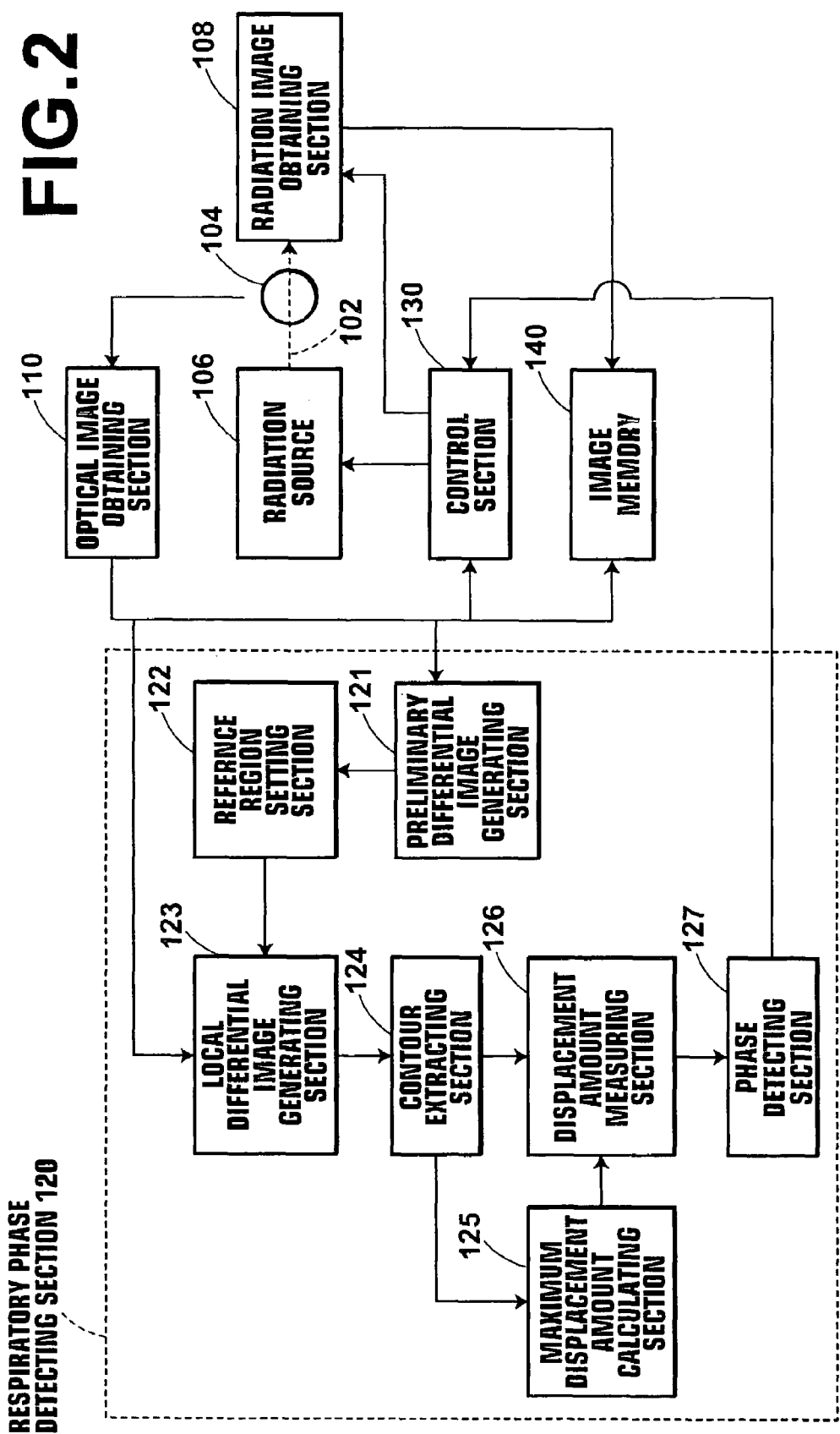
FIG. 2 is a block diagram of the radiographing system 100 illustrating one example of configuration thereof.

FIG. 1 is an external view of a radiographing system 100 illustrating one aspect of the external view thereof. FIG. 2 is a block diagram of the radiographing system 100 of the present invention illustrating one example of configuration thereof.

The radiographing system 100 comprises: a radiation source 106 for emitting radiation rays 102 to a test subject 104; a radiation image obtaining section 108 for obtaining radiation images P1 to Pm (m denotes an intended number of respiratory phases to be described later) of the test subject 104 by detecting radiation rays emitted from the radiation source and transmitted through the test subject 104; and an optical image obtaining section 110 for sequentially obtaining optical image Fi (i denotes an arbitrary frame number) of the test subject 104 having the contour that varies with respiration of the subject by imaging the subject continuously. The system further comprises: a respiratory phase detecting section 120 for detecting a respiratory phase Ti of the test subject 104 simultaneously with the optical imaging described above based on the contour of the subject on the optical image Fi obtained by the optical image obtaining section 110; a control section 130 for controlling the radiation source 106 such that the radiation rays 102 are emitted to the test subject 104 when the respiratory phase Ti detected by the respiratory phase detecting section corresponds to intended respiratory phases Td1 to Tdm during the optical imaging of the test subject 104; and an image memory 140 for storing various images including the radiation image Pi obtained by the radiation image obtaining section 108 and optical image Fi obtained by the optical image obtaining section 110.

The optical image obtaining section 110 is configured also to function as an optical image obtaining section for obtaining a plurality of preliminary optical images Fp1, Fp2, ..., Fpn (n denotes the number of preliminary optical images obtained) in advance by imaging the test subject 104 continuously at least during the time period from either a maximum inhaled or exhaled state of the test subject 104 to the other, apart from functioning as the optical image obtaining section for what is called as the real imaging in which the respiratory phase Ti of the test subject 104 is actually detected.

The respiratory phase detecting section 120 comprises: a preliminary differential image generating section 121 for generating preliminary differential images Sp12, Sp23, ..., Sp(n−1) (n) by performing a subtractive operation between each pair of temporally successive optical images of the plurality of preliminary optical images Fp1 to Fpn, that is, between Fp1 and Fp2, Fp2 and Fp3, ..., and between Fpn−1 and Fpn; a reference region setting section 122 for setting a local region on the optical image Fi corresponding to a local region Rp that includes a differential region having the largest area among the differences represented by each of the preliminary differential images Sp12 to Sp (n−1) (n) as a reference region R; and a local differential image generating section 123 for generating a preliminary local differential image Scp (t−1) (t) (2≦t≦n) or local differential image Sc (i−1) (i) (2≦i) that represents the difference between the images within the reference region of two temporally successive preliminary optical images Fpt−1 and Fpt (2≦t≦n) or of two temporally successive optical images Fi−1 and Fi (2≦i) obtained by the optical image obtaining section 110 by performing a subtractive operation between them. The respiratory phase detecting section 120 further comprises: a contour extracting section 124 for extracting a preliminary contour Cpt or a contour Ci that varies with the respiration of the test subject from the reference region on the preliminary optical image Fpt or on the optical image Fi based on the difference represented by the preliminary local differential image Scp (t−1)(t) or local differential image Sc (i−1) (i); a maximum displacement amount calculating section 125 for calculating a maximum amount of displacement Dmax of the preliminary contour Cpt based on the plurality of preliminary optical images Fp1 to Fpn; a displacement amount measuring section 126 for sequentially detecting the displacement direction Vi of the contour Ci on the optical image based on the time-series optical image Fi obtained by the optical image obtaining section 110, and sequentially measuring the amounts of displacement Di of the contour Ci with reference to the position of the contour at the moment when the displacement direction is reversed; and a phase detecting section for detecting the respiratory phase Ti of the test subject 104 based on the relationship of the amount of displacement Di of the contour Ci to the maximum amount of displacement Dmax.

In the present embodiment, the radiation image obtaining section 108 uses a flat panel detector that detects radiation rays transmitted through the test subject 104, and directly converts the radiation image information to electrical signals, and the optical image obtaining section 110 uses a CCD camera that obtains an optical image by detecting visible lights. Preferably, the optical image obtaining section 110 is disposed in a place which is in substantially the same direction as the radiation source 106 relative to the test subject 104. The radiation ray may be x-ray, α-ray, β-ray, γ-ray, or the like. The intended respiratory phase Td is assumed to be a plurality of respiratory phases included in a respiratory cycle of maximum inhaled to exhaled state of the test subject.

In the present embodiment, assumptions are made that the optical image obtaining section 110 is to image the upper body of the test subject 104 from the rear side, and a chest radiation image of the test subject 104 is to be obtained with the radiation source 106 and radiation image obtaining section 108.

Figure 3:
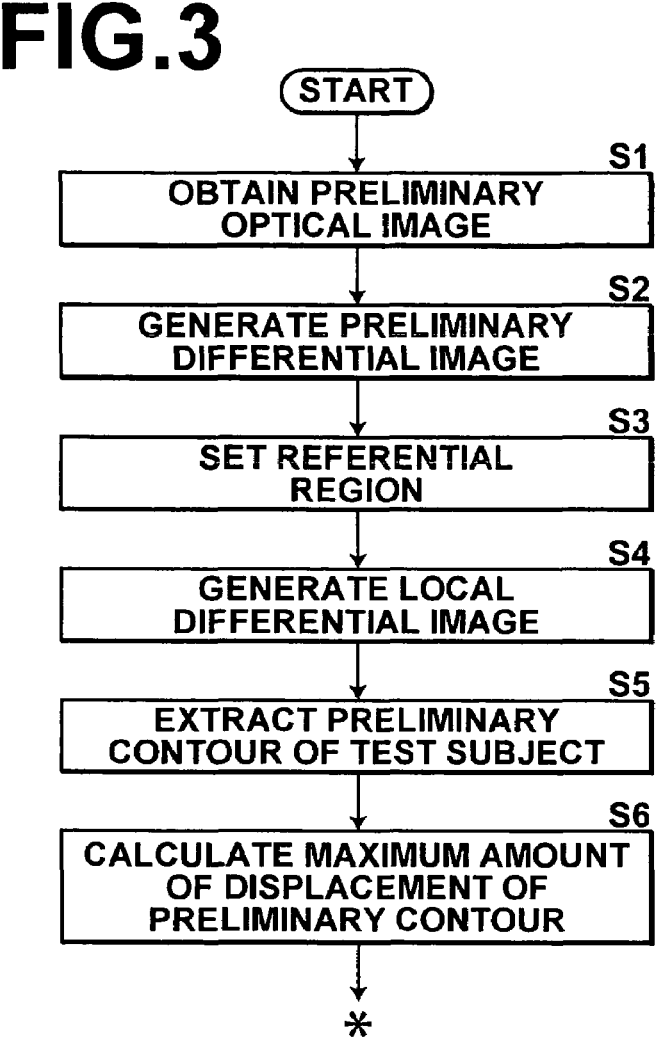
FIG. 3 is a flow diagram of the radiographing system 100 illustrating the process flow thereof (former half).
Figure 4:
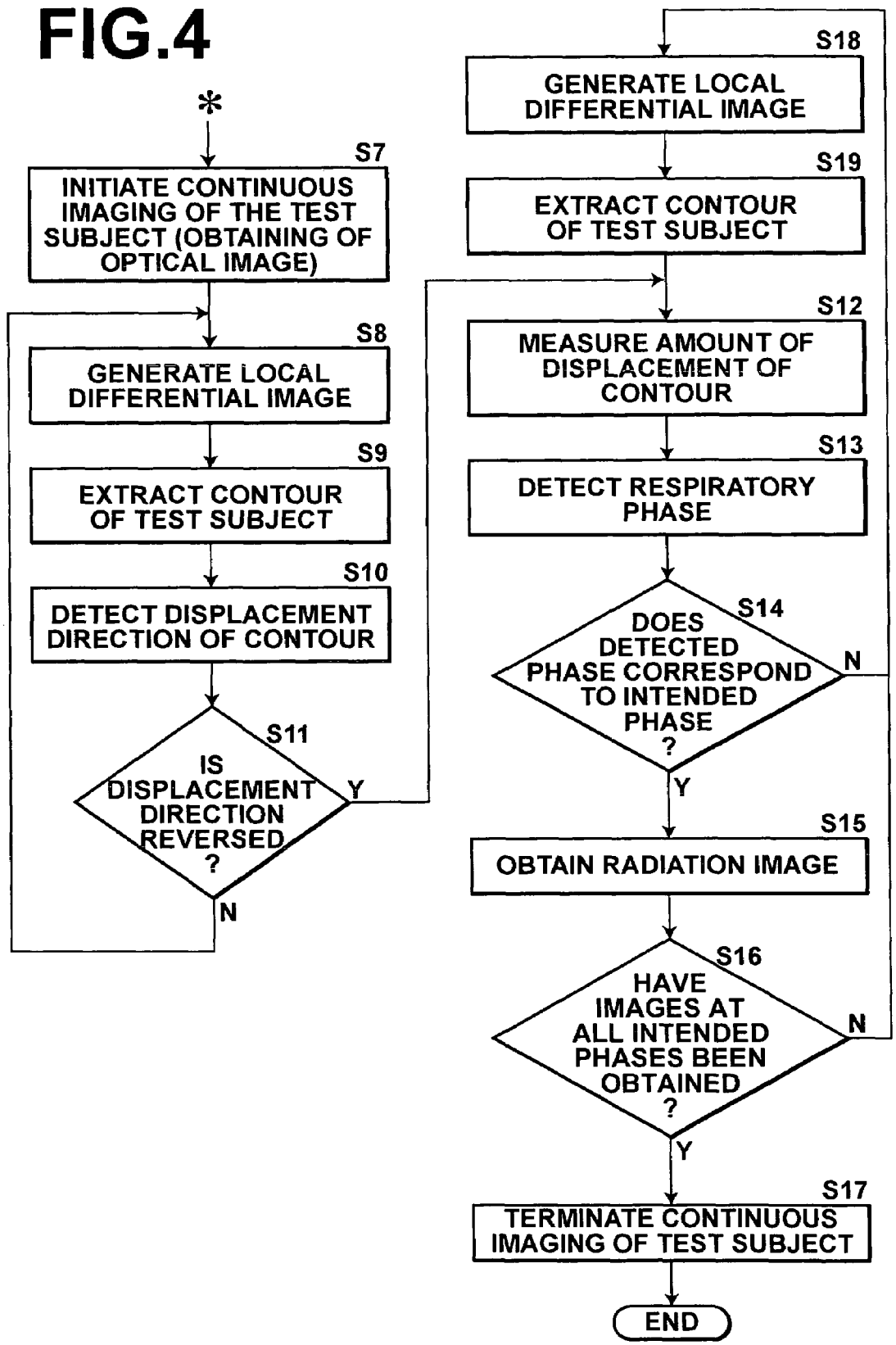
FIG. 4 is a flow diagram of the radiographing system 100 illustrating the process flow thereof (latter half).

Hereinafter, the operation of the radiographing system 100 according to the present embodiment will be described. FIGS. 3 and 4 are drawings illustrating the former and latter halves of the process flow of the system respectively.

First, determination is made where to set the reference region R. That is, determination is made on which part of the contour of the test subject 104 is referenced to detect the respiratory phases of the test subject 104.

The optical image obtaining section 110 obtains a plurality of preliminary optical images Fp1 to Fpn in advance by imaging the upper body of the test subject 104 continuously from the rear side at least during the time period from either a maximum inhaled or exhaled state of the test subject 104 to the other (step S1). For example, the preliminary optical images are obtained during the time period in which the test subject 104 repeats exhaling and inhaling around three cycles. Preferably, the imaging frame rate is in the range from about 3 to about 10 f/s (frames per second). The preliminary optical images Fp1 to Fpn obtained in this manner are stored sequentially in the image memory 140.

Figure 5:
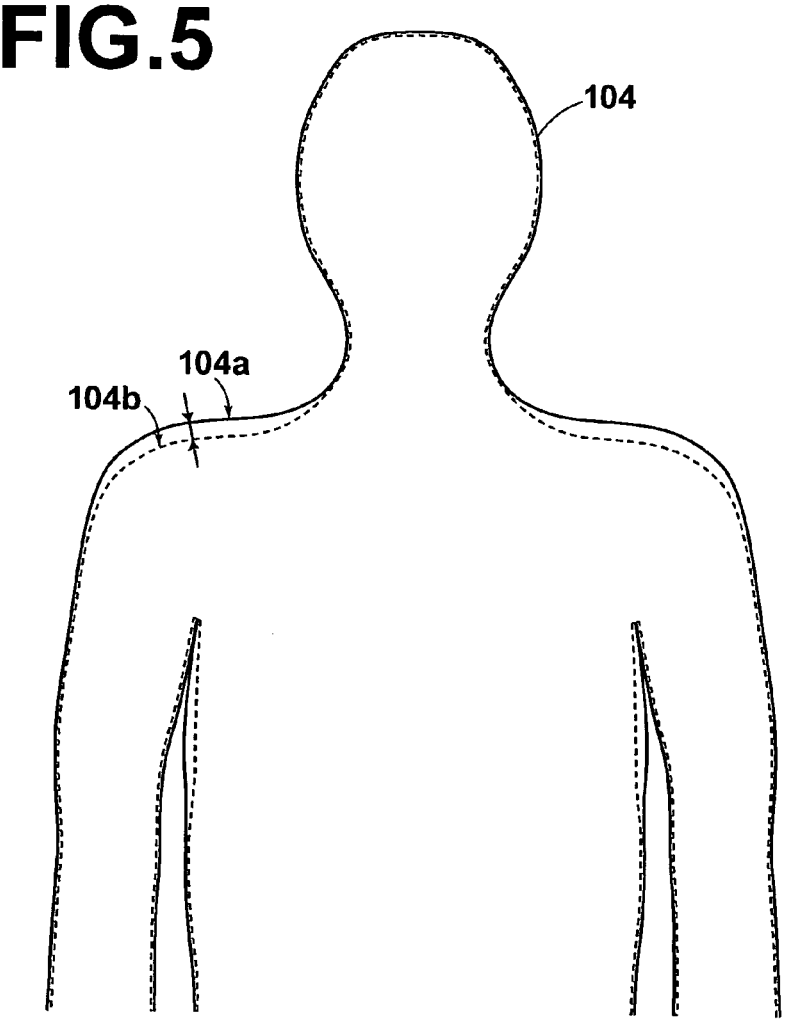
FIG. 5 is a drawing of a test subject 104 illustrating the contours thereof at maximum inhaled and exhaled states.

As shown in FIG. 5, the contour of the upper body of the test subject 104 moves to the outermost points (104a) at a maximum inhaled state, and moves to the innermost points (104b) at a maximum exhaled state. Consequently, each of the plurality of preliminary optical images Fp1 to Fpn has the upper body of the test subject 104 having a slightly different contour with each other varied with the respiration, which includes information that may be used for identifying the maximum amount of displacement Dmax of the contour (variation range).

Figure 6:
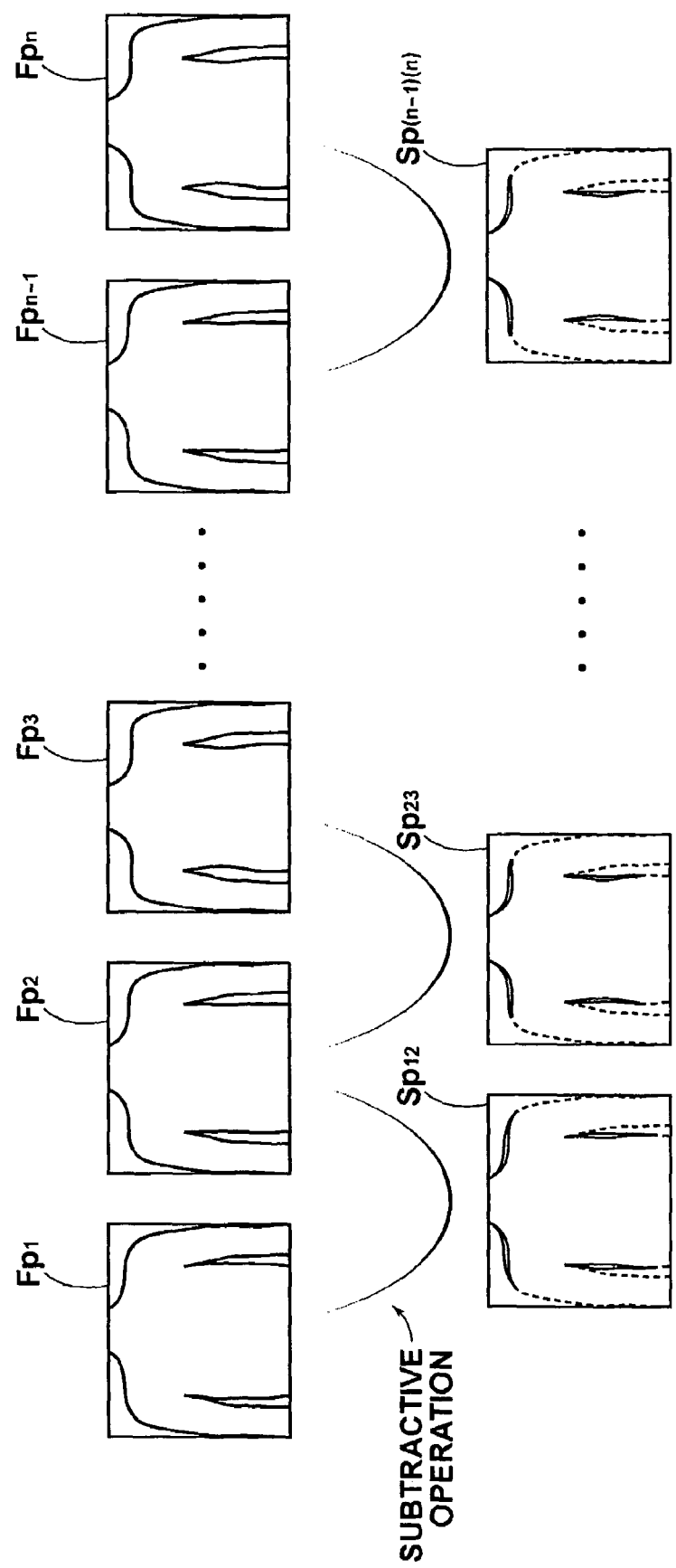
FIG. 6 is a drawing illustrating the relationship between preliminary optical images and preliminary differential images.

The preliminary differential image generating section 121 reads out the plurality of preliminary optical images Fp1 to Fpn from the image memory 140, and performs a subtractive operation between each pair of temporally successive preliminary optical images Fpt-1 and Fpt to generate a preliminary differential image Sp (t-1) (t) that represents the difference between them (step S2). That is, if n preliminary optical images Fp1, Fp2, Fp3, . . . , and Fpn are assumed to have been obtained with time, subtractive operations are performed between Fp1 and Fp2, Fp2 and Fp3, and between Fpn-1 and Fpn to generate preliminary subtractive images Sp12, Sp23, . . . , and Sp(n-1) (n), each representing the difference between each of the image pairs. The preliminary differential images are stored in the image memory 140. FIG. 6 is a drawing illustrating the relationship between the plurality of preliminary optical images Fp1 to Fpn and each of the preliminary differential images Sp12 to Sp(n-1) (n).

Figure 7:
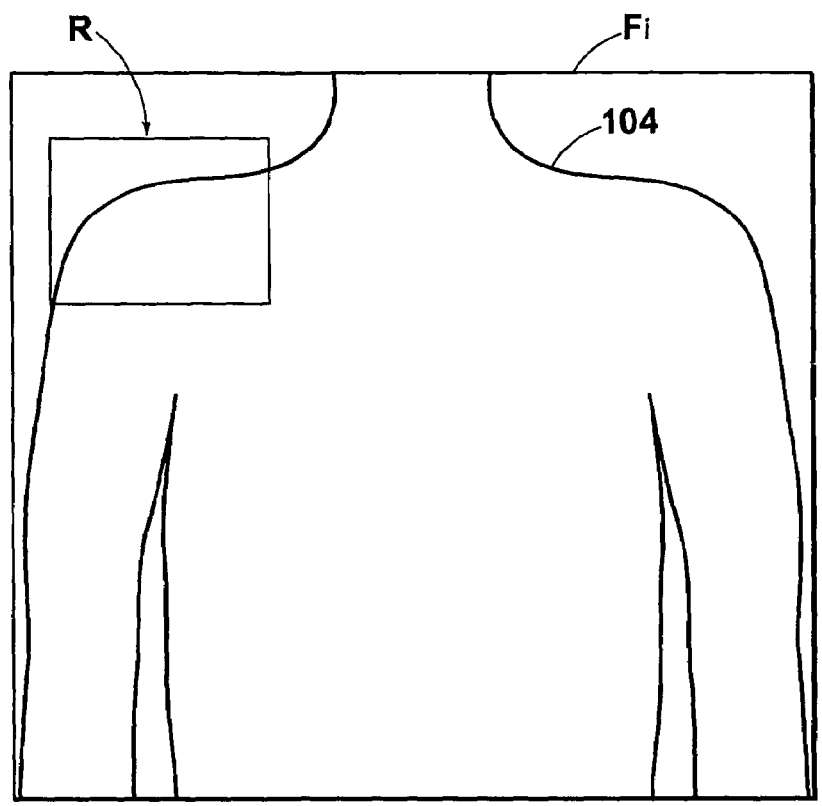
FIG. 7 is a drawing illustrating a reference region R set on an optical image.

The reference region setting section 122 reads out the preliminary differential images Sp12 to Sp (n-1) (n), extracts a local region Rp that includes the differential region having the largest area among the differences represented by each of the preliminary differential images, and sets a local region on the optical image corresponding to the local region Rp as the local reference region R (step S3). The reason for this is that the region adjacent to the differential region having the largest area may be deemed as the place where the change in the contour of the test subject 104 becomes maximal. Thus, selection of the reference region R in this manner allows the extraction of the contour of the test subject 104 from the optical image with high resolution, and the accuracy for detecting the respiratory phases is maximized. The reference region setting method for setting the reference region R is not limited to the aforementioned method in which the reference region R is set based on the analysis result of the preliminary optical images Fp1 to Fpn. For example, an appropriate region based on the empirical rule is preset and selected as the reference region, or it may be set manually. FIG. 7 is a drawing illustrating the reference region R set on an optical image F by one of the methods described above. Here, the shoulder of the test subject 104 is set as the reference region R.

When the reference region R is set, the local differential image generating section 123 performs a subtractive operation between the images within the reference region of two temporally successive preliminary optical images Fpt-1 and Fpt obtained by the optical image obtaining means 110 to generate a local differential image Spc (t-1) (t) that represents the difference between them (step S4), and the contour extracting section 124 extracts a preliminary contour Cpt that varies with respiration of the test subject 104 from the reference region R on the preliminary optical image Fpt based on the difference represented by the local differential image Spc(t-1)(t)(step S5). For example, the difference may be approximated by the line segment in the longitudinal direction of the difference, and the line segment may be deemed to be the preliminary contour Cpt of the test subject 104. Then, the maximum displacement amount calculating section 125 detects the displacement direction Vp of the preliminary contour Cpt and calculates the maximum amount of displacement Dmax of the preliminary contour Cpt based on the plurality of preliminary optical images Fp1 to Fpn (step S6). The maximum amount of displacement Dmax is used at a later step for obtaining the respiratory phase Ti of the test subject 104 based on the amount of displacement D of the contour Ci of the test subject 104 on the optical image Fi.

Thus far are the preliminary steps, and now the process will move into the steps for detecting the respiratory phase Ti of the test subject 104 in real time, and obtaining the radiation images P1 to Pm of the test subject 104 at each of the intended respiratory phases Td1 to Tdm.

First, continuous imaging of the test subject 104 is initiated by the optical image obtaining means 110 (step S7). That is, the optical image obtaining means 110 takes the images of the test subject 104 continuously at the imaging rate of 3 to 10 f/s to sequentially obtain the optical image Fi, and stores it in the image memory 140. The optical image Fi is stored in the image memory 140 with the frame number i related thereto to indicate in which order the optical image Fi is obtained.

When one optical image Fi of the test subject 104 is obtained and stored in the image memory 140 by the optical image obtaining means 110, the local differential image generating section 123 reads out the latest two temporally successive optical images Fi-1 and Fi from the image memory 140, and performs a subtractive operation between the two images within the reference region R of the two optical images to generate a local differential image Sc(i-1) (i) that represents the difference between them. Then, it stores the local differential image Sc(i-1) (i) in the image memory 140 with the frame numbers (i-1) and (i) related thereto, which indicate the optical images involved in the subtractive operation (step S8). If only a single image is stored in the image memory 140, the local differential image generating section 123 stands by until two images have been obtained and stored in the image memory 140.

When the local differential image Sc(i-1) (i) is generated, the contour extracting section 124 reads out the latest two local differential images Sc (i-2) (i-1) and Sc(i-1) (i) from the image memory 140, and extracts contours Ci-1 and Ci that vary with respiration of the test subject 104 from the respective local differential images (step S9). If only a single local differential image is stored in the image memory 140, the contour extracting section 124 stands by until two local differential images have been generated and stored in the image memory 140. The contour Ci-1 extracted in the past may have been stored, and used instead of re-extracting it.

When the contours Ci-1 and Ci are extracted, the displacement amount measuring section 126 detects the displacement direction Vi, that is, the direction to which the contour is moving with time is detected based on the extracted two contours (step S10).

When the displacement direction Vi of the contour is detected, the displacement amount measuring section determines if the displacement direction Vi of the contour detected in step S10 is reversed to a predetermined direction corresponding to an inhaling or exhaling state (e.g. inhaling state corresponds to the direction from the center of the image to outward) which differs from the previous displacement direction vi−1 (step S11). If it is determined that the direction has been reversed to the predetermined direction, the process flow moves to step S12. If not or if there is no displacement direction information obtained previously, the process flow returns to step S7, and obtains an optical image corresponding to the next frame with the subscript i incremented by one (i=i+1).

In step 12, the displacement amount measuring section 126 measures the amount of displacement Di of the contour Ci with reference to the position of the contour at the moment when the displacement direction of the contour is reversed (step S12).

Then, the phase detecting section 127 detects the respiratory phase Ti based on the relationship of the current amount of displacement Di of the contour Ci to the maximum amount of displacement Dmax already obtained (step S13). For example, in the case where the amount of displacement of the contour is measured with reference to the position of the contour at the moment when the displacement direction is reversed from the direction toward the center of the image to the outward, and the maximum amount of displacement Dmax is 100 pixels. If the current amount of displacement Di is 10 pixels, then the current respiratory phase Ti may be detected as the respiratory phase which is in ahead of the maximum exhaled state by 1/10 of the respiratory cycle.

Control section 130 determines if the detected respiratory phase Ti corresponds to any respiratory phase Tdk ($1 \leq k \leq m$) of the intended respiratory phase Td1 to Tdm (step S14). If the determination result is positive, the control section 130 sends out a control signal Y1 to the radiation source 106 to emit radiation rays 102 to the test subject 104, and a control signal Y2 to the radiation image obtaining section 108 to obtain a radiation image Pk of the test subject at the time and to store it in the image memory 140 (step S15). On the other hand, if the detected respiratory phase Ti does not correspond to any of the intended respiratory phases Td1 to Tdm, the process flow moves to step S18.

In step S18, when one optical image Fi corresponding to the next image frame of the test subject 104 is obtained with the suffix i incremented by 1 (i=i+1), and stored in the image memory 140, the local differential image generating section 123 reads out the latest two temporally successive optical images Fi−1 and Fi from the image memory 140, and performs a subtractive operation between the two images within the reference region R of the two optical images to generate a local differential image Sc(i−1) (i) that represents the difference between them. Then, it stores the local differential image Sc(i−1) (i) in the image memory 140 with the frame numbers (i−1) and (i) related thereto, which indicate the optical images involved in the subtractive operation (step S18).

When the local differential image Sc(i−1) (i) is generated, the contour extracting section 124 reads out the latest two local differential images Sc(i−2) (i−1) and Sc(i−1) (i) from the image memory 140, and extracts partial contours Ci−1 and Ci of the test subject 104 from the respective local differential images (step S19). When the contours Ci−1 and Ci are extracted, the process flow returns to step S12.

In step S15, when a radiation image P of the test subject 104 is obtained, the control section 130 determines if all the radiation images P1 to Pm, each corresponding to each of the intended respiratory phases Td1 to Tdm, have been obtained (step S16). If the determination result is positive, the imaging of the test subject is terminated (step S17), and the process flow is closed. If negative, it returns to step S18.

In the manner described above, the steps are repeated until all the radiation images P1 to Pm, each corresponding to each of the intended respiratory phases Td1 to Tdm, have been obtained.

As has been describe, according to the present embodiment of radiographing system 100 having the radiation emission control apparatus of the present invention, the respiratory phase Ti of the test subject 104 is detected using optical image Fi obtained without any radiation exposure to the test subject 104. Thus, the radiation exposure to the test subject is limited only when the subject is actually radiographed, unlike the method in which a dynamic radiation image is obtained by emitting additional radiation to the test subject to detect the respiratory phases of the test subject. Further, the system detects the respiratory phases Ti of the test subject 104 based on the displacement of the contour Ci of the test subject 104 on the optical images Fi. Thus, the system may prevent detection errors of the respiratory phases Ti arising from the changes in the posture of the test subject 104, unlike the method in which an amount of displacement on the body surface of the test subject is directly measured with a distance measuring means having an LED, LD or the like to detect the respiratory phases of the test subject. Consequently, the system may detect the respiratory phases Ti of the test subject 104 with constant accuracy and emit radiation rays 102 to the test subject 104 in synchronization with the intended respiratory phases Td1 to Tdm, while minimizing the radiation exposure to the test subject 104.

In the present embodiment, in detecting the amount of displacement Di of the contour Ci, the reference of the displacement is fixed at the position of the contour at the moment when the displacement direction is reversed. Alternatively, for example, the reference may be altered by resetting it every time when the detected respiratory phase Ti corresponds to one of the intended respiratory phases Td1 to Tdm based on the position of the contour at the time. By resetting the reference position in the manner described above, it is expected that the detection errors of the respiratory phases Ti, which may arise from the changes in the posture of the test subject 104 during the imaging, may be minimized.

Further, in the present embodiment, the contour Ci of the test subject 104 is extracted based on the local differential image Sp(i−1) (i). Alternatively, it may be extracted directly from the optical image Fi through an edge detecting process or the like.

Figure 8:
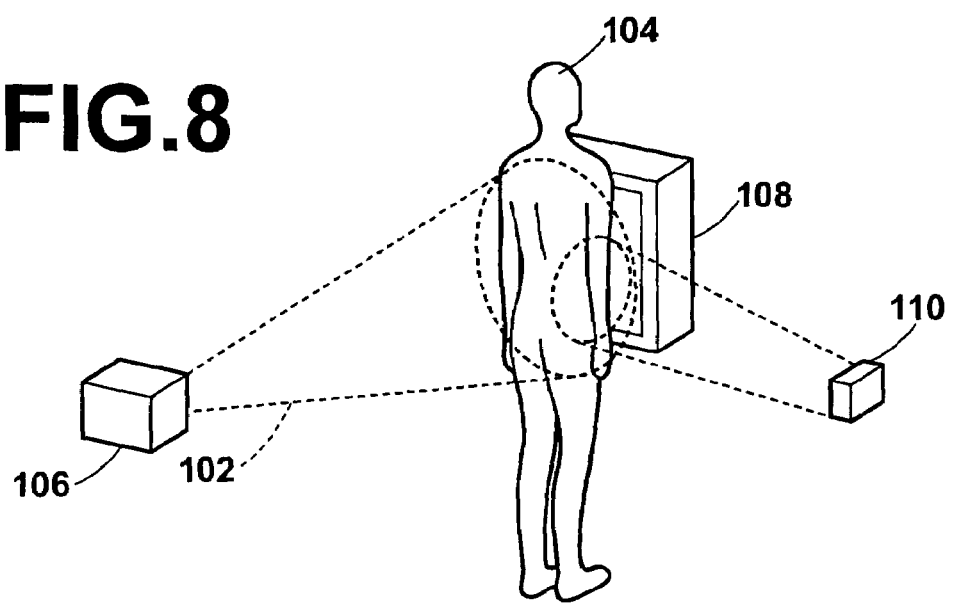
FIG. 8 is a drawing illustrating an embodiment of the radiographing system 100 in which optical images are obtained by imaging the abdominal region of a test subject from a lateral side.
Figure 9:
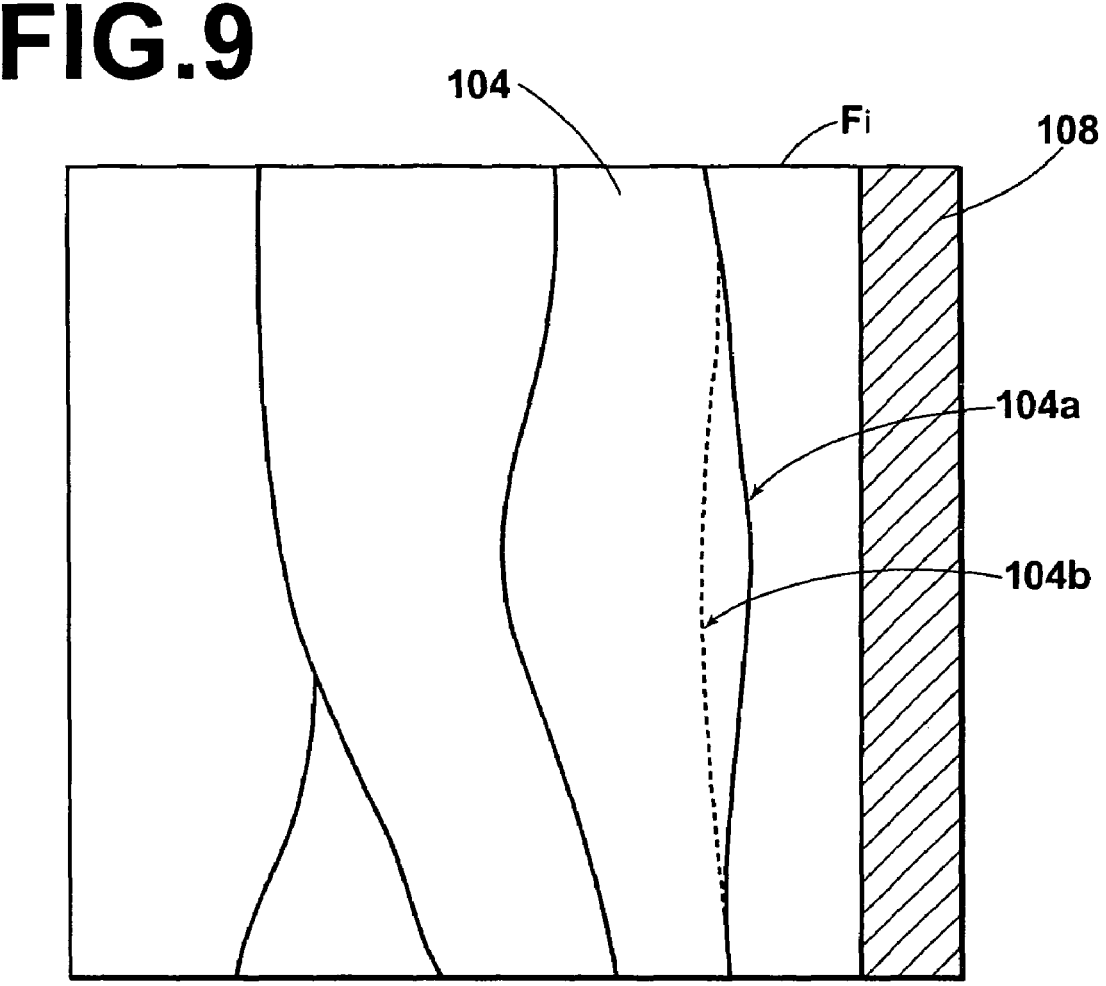
FIG. 9 is a drawing illustrating a sample image obtained by imaging a test subject from a lateral side.

Still further, in the present embodiment, the upper body of the test subject 104 is imaged from the rear side, and the respiratory phase Ti is detected according to the displacement of the contour of the shoulder. Alternatively, for example, the abdominal region of the test subject may be imaged from a lateral side, and the respiratory phase Ti of the test subject may be detected according to the displacement of the surface of the abdominal region (or back) of the test subject 104, as shown in FIG. 8. In this case, the contour of the abdominal surface varies greatly, and it may be readily figured out that which part of the region varies the most, so that a predetermined local region corresponding to the abdominal region may be preset as the reference region R, instead of searching for the reference region R as in the present embodiment. Such an optical image Fi obtained by imaging the abdominal region in the manner described above is shown in FIG. 9. The test subject 104 has the abdominal contour of 104a when it is in a maximum inhaled state and that of 104b when it is in a maximum exhaled state.

What is claimed is:

1. A radiation emission control method in which optical images are obtained using a radiation emission control apparatus, comprising:

sequentially obtaining optical images of a test subject having a geometric feature that varies at least partially with respiration of the subject by imaging the subject continuously;

sequentially detecting respiratory phases of the test subject simultaneously with the optical imaging based on the geometric feature of the subject on the optical images;

emitting radiation rays to the test subject with a radiation source; and controlling the radiation source such that radiation rays are emitted to the test subject when the detected respiratory phase corresponds to an intended respiratory phase during the optical imaging of the subject, wherein a plurality of preliminary optical images are obtained in advance by imaging the test subject continuously at least during the time period from either a maximum inhaled or exhaled state of the test subject to the other; and the respiratory phase detecting comprises:

extracting a contour that varies with respiration of the test subject from a predetermined local reference region of the preliminary optical images and optical images;

calculating a maximum amount of displacement of the contour in the plurality of preliminary optical images;

sequentially detecting the displacement directions of the contour on the optical images based on the plurality of preliminary optical images, and sequentially measuring the amounts of displacement of the contour with reference to the position of the contour at the moment when the displacement direction is reversed; and detecting respiratory phases of the test subject based on the relationship of the amounts of displacement of the contour to the maximum displacement amount.

2. A radiation emission control apparatus, comprising:

an optical image obtaining means for sequentially obtaining optical images of a test subject having a geometric feature that varies at least partially with respiration of the subject by imaging the subject continuously;

a respiratory phase detecting means for sequentially detecting respiratory phases of the test subject simultaneously with the optical imaging based on the geometric feature of the subject on the optical images;

a radiation source for emitting radiation rays to the test subject; and a control means for controlling the radiation source such that radiation rays are emitted to the test subject when the respiratory phase detected by the respiratory phase detecting means corresponds to an intended respiratory phase during the optical imaging of the subject, wherein the optical image obtaining means is configured to obtain a plurality of preliminary optical images in advance by imaging the test subject continuously at least during the time period from either a maximum inhaled or exhaled state of the test subject to the other; and the respiratory phase detecting means comprise:

a contour extracting means for extracting a contour that varies with respiration of the test subject from a predetermined local reference region of the preliminary optical images and optical images;

a maximum displacement amount calculating means for calculating a maximum amount of displacement of the contour in the plurality of preliminary optical images;

a displacement amount measuring means for sequentially detecting the displacement directions of the contour on the optical images based on the time-series optical images obtained by the optical image obtaining means, and sequentially measuring the amounts of displacement of the contour with reference to the position of the contour at the moment when the displacement direction is reversed; and a phase detecting means for detecting respiratory phases of the test subject based on the relationship of the amounts of displacement of the contour to the maximum displacement amount.

3. The radiation emission control apparatus according to claim 2, wherein:

the contour extracting means comprises a local differential image generating means constructed to perform a subtractive operation between images within the predetermined reference region of two temporally successive optical images obtained by the optical image obtaining means to generate a local differential image that represents the difference between the images; and the contour extracting means is configured to extract the contour based on the difference represented by the local differential image.

4. The radiation emission control apparatus according to claim 3, wherein the respiratory phase detecting means further comprises:

a preliminary differential image generating means constructed to perform a subtractive operation between each pair of two temporally successive preliminary optical images of the plurality of preliminary optical images to generate preliminary differential images, each representing the difference between each image pair; and a reference region setting means constructed to set a local region of the optical images that corresponds to the local region of the differential images that includes a differential region having the largest area among the differences represented by each preliminary differential image as the reference region.

5. The radiation emission control apparatus according to claim 3, wherein the intended respiratory phase is a plurality of respiratory phases included in a respiratory cycle of maximum inhaled to exhaled state of the test subject.

6. The radiation emission control apparatus according to claim 2, wherein the respiratory phase detecting means further comprises:

a preliminary differential image generating means constructed to perform a subtractive operation between each pair of two temporally successive preliminary optical images of the plurality of preliminary optical images to generate preliminary differential images, each representing the difference between each image pair; and a reference region setting means constructed to set a local region of the optical images that corresponds to the local region of the differential images that includes a differential region having the largest area among the differences represented by each preliminary differential image as the reference region.

7. The radiation emission control apparatus according to claim 2, wherein the intended respiratory phase is a plurality of respiratory phases included in a respiratory cycle of maximum inhaled to exhaled state of the test subject.

8. The radiation emission control apparatus according to claim 2, wherein the intended respiratory phase is a plurality of respiratory phases included in a respiratory cycle of maximum inhaled to exhaled state of the test subject.

9. The radiation emission control apparatus according to claim 2, wherein the geometric feature is a shadow region of the test subject.

10. The radiation emission control apparatus according to claim 2, wherein the geometric feature is a marker arranged on the test subject.

11. The apparatus of claim 10 wherein the marker comprises a cloth draped over a contour surface of the test subject.

12. The radiation emission control apparatus according to claim 2, wherein the contour extracting means is constructed to extract the contour of the abdominal region of the test subject.

13. The radiation emission control apparatus according to claim 2, wherein the contour extracting means is constructed to extract the contour of the shoulder of the test subject.

14. The apparatus of claim 2 wherein the maximum displacement corresponds to a geometric configuration of a subject during a maximum inhale state.

15. The apparatus of claim 2 wherein the maximum displacement corresponds to a geometric configuration of a subject during a maximum exhale state.

16. A program embodied on a recordable medium for causing a computer to perform the functions of:
    sequentially receiving optical images of a test subject having a geometric feature that varies at least partially with respiration of the subject obtained by imaging the subject continuously, and sequentially detecting respiratory phases of the test subject based on the geometric feature of the subject on the optical images; and
    controlling a radiation source such that radiation rays are emitted to the test subject when the detected respiratory phase corresponds to an intended respiratory phase during the optical imaging of the subject;
    wherein a plurality of preliminary optical images are obtained in advance by imaging the test subject continuously at least during the time period from either a maximum inhaled or exhaled state of the test subject to the other; and
    the respiratory phase detecting comprises:
    extracting a contour that varies with respiration of the test subject from a predetermined local reference region of the preliminary optical images and optical images;
    calculating a maximum amount of displacement of the contour in the plurality of preliminary optical images;
    sequentially detecting the displacement directions of the contour on the optical imagings based on the plurality of preliminary optical images, and sequentially measuring the amounts of displacement of the contour with reference to the position of the contour at the moment when the displacement direction is reversed; and
    detecting respiratory phases of the test subject based on the relationship of the amounts of displacement of the contour to the maximum displacement amount.

* * * * *